United States Patent [19]

Carcia et al.

[11] Patent Number: 4,469,640
[45] Date of Patent: Sep. 4, 1984

[54] CATALYTIC CONVERSION OF FORMAMIDES TO ISOCYANATES

[75] Inventors: Peter F. Carcia, Wilmington, Del.; George E. Heinsohn, Elkton, Md.; Velliyur N. M. Rao, Wilmington, Del.

[73] Assignee: E. I. Du Pont de Nemours and Company, Wilmington, Del.

[21] Appl. No.: 475,032

[22] Filed: Mar. 14, 1983

[51] Int. Cl.³ .......................................... C07C 118/00
[52] U.S. Cl. ................................................. 260/453 P
[58] Field of Search ..................................... 260/453 P

[56] References Cited

U.S. PATENT DOCUMENTS 4,046,712 9/1977 Cairns et al. ..................... 252/447
4,207,251 6/1980 Heyboer ........................... 260/453 P

FOREIGN PATENT DOCUMENTS 1537839 1/1970 United Kingdom .
1455248 11/1976 United Kingdom .

OTHER PUBLICATIONS

S. K. Sharm & J. Spitz, Thin Solid Films, 61, L13–L15, (1979).
A. E. Presland et al., Progress in Surface Science, 3, 63 (1973).
B. Abeles et al., Advanced Physics, 24, 407 (1975).

Primary Examiner—Dolph H. Torrence

[57] ABSTRACT

Monomethylformamide is converted to methyl isocyanate by reaction with oxygen in the presence of an inert diluent gas at 300°–600° C. using as catalyst sputtered silver or silver/gold on an inert, hard, nonporous support.

5 Claims, No Drawings

CATALYTIC CONVERSION OF FORMAMIDES TO ISOCYANATES

BACKGROUND OF THE INVENTION

1. Field of the Invention

The present invention relates to the production of isocyanates, preferably methyl isocyanate. At present methyl isocyanate is produced in the United States by phosgenation of monomethylamine followed by decomposition of the resulting carbamyl chloride to methyl isocyanate and hydrogen chloride.

2. Prior Art

U.S. Pat. No. 4,207,251 discloses the oxidation of N-alkylformamides to the corresponding isocyanates over precious metal catalysts including silver.

SUMMARY OF THE INVENTION

The present invention relates to an improved process of converting formamides of the formula $R(NHCHO)_n$ where R is an organic group and n is 1 or 2 to the corresponding isocyanate over a silver or silver/gold catalyst wherein the silver or silver/gold is sputtered or ion plated on an inert support. Such catalysts give a higher productivity of isocyanate. When measured as g of product/g of silver/hr, productivity increases by more than a factor of 50 as compared with conventional silver crystal or silver wool catalysts.

DETAILED DESCRIPTION

The catalyst used in the present invention is sputtered or ion plated silver or silver/gold on an inert support. Generally the metal or metal alloy will comprise from 0.05-50 weight percent of the total catalyst composition. Generally the catalyst support will be a hard, non-porous refractory particulate material having a mean particle diameter in the range of from 0.1 micron to 0.5 centimeter. Generally the support should have a surface area below about 20 square meters per gram and preferably less than 3 square meters per gram. Generally the support will be a ceramic material. Alumina and silica are the preferred catalyst supports although other oxides such as ceria, yttria, zirconia or titania can be used.

The catalysts of the invention were prepared by physical vapor deposition where evaporated metal was allowed to deposit on a silica support which was biased electrically or by RF sputtering. In the latter method, fused silica particles which pass a 30 mesh (U.S. Sieve Series) screen and are retained on a 50 mesh (U.S. Sieve Series) screen were distributed in several pyrex dishes on a rotating substrate table beneath a silver target or gold/silver target and coated with the metal or metals. The particulate substrates were periodically mixed outside the sputtering chamber to ensure uniformity.

Generally the process of the present invention is carried out at from 300°-600° C. with from 400°-500° C. being the preferred range. Under comparable conditions when using silver wool where it is possible to have hot spots, the catalysts of the invention offer a more uniform distribution of small amounts of the metal or metal alloy on the support which results in a higher selectivity to methyl isocyanate.

The reaction is carried out in the gas phase in the presence of an inert gas such as nitrogen, carbon dioxide, helium, neon, argon or xenon. Nitrogen is the preferred carrier gas because it is inexpensive, but helium is used in some of the Examples to facilitate product analysis by gas chromatography. Generally the proportion of methylformamide in the reaction mixture at the start should be from 0.1-40 volume percent. There should be oxygen present in the reaction mixture for carrying out the reaction. The amount of oxygen present in the feed to the reactor is generally from 0.1-20 volume percent.

The pressure used is not particularly critical and may be varied from $<1 \times 10^5$ Pa to $1 \times 10^6$ Pa or higher. For operational reasons it is most preferred that the reaction be carried out at an absolute pressure of 1 atmosphere.

The present invention is applicable to N-monosubstituted formamides of the formula

where R is an unsubstituted hydrocarbon group or substituted hydrocarbon group, generally containing not more than 18 carbon atoms, including substituted or unsubstituted alkyl groups, cycloalkyl groups, aryl groups, preferably phenyl, aralkyl groups or alkaryl groups, where the substituents may be, for example, chlorine, fluorine, cyanogen and alkyl carbonyl or alkoxyl carbonyl, preferably containing not more than 10 carbon atoms in the alkyl or alkoxy groups, and where n is 1 or 2.

Methyl isocyanate is used in the production of certain insecticides and nematicides including s-methyl-N-[(methylcarbamoyl)oxy] thioacetimidate (methomyl), an insecticide.

EXAMPLES

In each of the Examples the catalyst was charged to a "U" shaped quartz tube reactor which had a 12 mm outside diameter. The reactor was brought to temperature in a sand bath under a flow of inert carrier gas. When the desired temperature is reached, oxygen flow is initiated and after about 2 minutes the monomethylformamide is introduced with sufficient carrier gas to achieve the desired composition. Total flow is such that the nominal residence time in the catalyst bed is about 0.2 second. After allowing one hour for equilibrium to be reached, samples are periodically withdrawn for analysis. In Examples 1-4 the gas flows reported are as measured at 0° C. and atmospheric pressure. Inert carrier gas and residual oxygen are excluded from the analysis and results are reported as molar percentages.

Example 1

Particulate silica of irregular shape which passes a 30 mesh (U.S. Sieve Series) screen and is retained on a 50 mesh (U.S. Sieve Series) screen is coated with 0.9 weight percent silver by ion plating to prepare the catalyst. The reactor is charged with 3.2 g of the catalyst and the bed heated to 470° C. Flows to the reactor are adjusted to 500 cc/minute of nitrogen, 20 cc/minute of oxygen an 5.76 ml/hour of liquid monomethylformamide. After reaching equilibrium, analysis of the effluent stream indicates a 43% conversion of monomethylformamide and a 78% selectivity for methyl isocyanate. This is equivalent to a production rate of 58.3 g methyl isocyanate per gram of silver per hour.

Example 2

Particulate silica of irregular shape which passes a 30 mesh (U.S. Sieve Series) screen and is retained on a 50 mesh (U.S. Sieve Series) screen is sputter coated with 4 weight percent silver to prepare the catalyst. The reactor is charged with 3.2 g of the catalyst and the bed heated to 470° C. Flows to the reactor are adjusted to 500 cc/minute of helium, 25 cc/minute of oxygen and 5.76 ml/hour of monomethylformamide. After reaching equilibrium, analysis of the effluent stream indicates an 85% conversion of monomethylformamide and a 75% selectivity for methyl isocynate. After 14 hours, both numbers begin to drop but then rise. After 30 hours of exposure, a conversion of 90% of monomethylformamide was achieved with 81% selectivity for methyl isocyanate. No further change in catalyst performance is noted during additional exposure. This is equivalent to a production rate of 25.3 g of methyl isocyanate per g of silver per hour.

Example 3

This Example is a comparison using silver crystals as the catalyst.

The reactor is charged with 8.4 g of silver crystals and heated to 470° C. Flows to the reactor are adjusted to 500 cc/minute of nitrogen, 20 cc/minute of oxygen and 5.76 ml/hour of liquid monomethylformamide. After reaching equilibrium, analysis indicates an 80% conversion of monomethylformamide and a 47% selectivity for methyl isocyanate. This is equivalent to a production rate of 0.2 g of methyl isocyanate per g of silver per hour.

Example 4

This Example is a comparison using silver wool as the catalyst.

The reactor is charged with 3.5 g of 0.03 mm O.D. silver wool and heated to 470° C. Flows to the reactor were adjusted to 500 cc/minute of helium, 25 cc/minute of oxygen and 5.76 ml/hour of liquid monomethylformamide. After reaching equilibrium, analysis indicated an 80% conversion of monomethylformamide and a 77% selectivity for methyl isocyanate. This is equivalent to a production rate of 1.0 g of methyl isocyanate per g of silver per hour.

Example 5

Example 1 was repeated with 37 cc/minute of monomethylformamide vapor, 25 cc/minute of oxygen from air and 475 cc/minute of nitrogen, fed as a mixture of air and nitrogen. Under these flow conditions two different sputter coated catalysts were evaluated at 470° C. and 500° C. After reaching equilibrium the product from the reactor was bubbled into an aqueous solution of monomethylamine to trap the isocyanate as 1,3-dimethylurea which was isolated after removal of excess of the trapping medium. The trapping period in all cases was 120 minutes and the conversion of the formamide >90%. Results are summarized in Table I. The Ag/Au on $SiO_2$ catalyst used in Table I was cosputtered with silica onto a silica support.

TABLE 1

| Catalyst | Wt. g. | Temp. °C. | Wt of Urea, g. |
|---|---|---|---|
| 4% Ag on $SiO_2$ | 2.6 | 470 | 13.5 |
| 4% Ag on $SiO_2$ | 2.6 | 500 | 13.9 |
| 1% Ag/Au on $SiO_2$ (87/13 atomic ratio) | 2.5 | 470 | 14.9 |
| 1% Ag/Au on $SiO_2$ (87/13 atomic ratio) | 2.5 | 500 | 12.5 |

The theoretical weight of urea for 100% conversion and 100% yield is 17.3 g.

We claim:

1. A process for preparing an isocyanate corresponding to the formula $$R(NCO)_n$$

where R is an unsubstituted alkyl group, cycloalkyl group, aryl group, aralkyl group or alkaryl group containing not more than 18 carbon atoms, or one of said groups substituted with chlorine, fluorine, cyanogen, alkyl carbonyl or alkoxy carbonyl containing not more than 10 carbon atoms in the alkyl or alkoxy group and n is 1 or 2 which (a) comprises contacting an N-monosubstituted formamide corresponding to the formula $$R(\underset{\underset{\mid}{N}}{\overset{H}{\mid}}-\underset{\underset{\parallel}{CH}}{\overset{O}{\parallel}})_n$$

where R and n are defined as above in the gas phase with an oxygen-containing gas in the presence of a catalyst formed of a particulate, hard nonporous refractory support on which has been deposited by physical vapor deposition from 0.5–50% by weight silver, or a silver/gold alloy.

2. The process of claim 1 wherein —R is —$CH_3$ and n is 1.

3. The process of claim 2 wherein the process is carried out at from 300°–600° C. using an inert carrier gas wherein 0.1–40 volume percent monomethylformamide is present in the feedstream to the reactor and from 0.1–20 volume percent oxygen is present in the feedstream to the reactor.

4. The process of claim 3 wherein the catalyst support is a ceramic material.

5. The process of claim 4 wherein the catalyst support is silica or alumina.

* * * * *